US012064595B2

United States Patent
Guala

(10) Patent No.: US 12,064,595 B2
(45) Date of Patent: Aug. 20, 2024

(54) FILTER FOR INFUSION MEDICAL LINES

(71) Applicant: INDUSTRIE BORLA S.P.A., Moncalieri (IT)

(72) Inventor: Gianni Guala, Turin (IT)

(73) Assignee: INDUSTRIE BORLA S.P.A, Moncalieri (IT)

( * ) Notice: Subject to any disclaimer, the term of this patent is extended or adjusted under 35 U.S.C. 154(b) by 864 days.

(21) Appl. No.: 17/040,286

(22) PCT Filed: Mar. 14, 2019

(86) PCT No.: PCT/IB2019/052079
§ 371 (c)(1),
(2) Date: Sep. 22, 2020

(87) PCT Pub. No.: WO2019/215516
PCT Pub. Date: Nov. 14, 2019

(65) Prior Publication Data
US 2021/0046243 A1 Feb. 18, 2021

(30) Foreign Application Priority Data
May 8, 2018 (IT) .......................... 102018000005165

(51) Int. Cl.
*A61M 5/165* (2006.01)
*A61M 5/38* (2006.01)
*A61M 39/10* (2006.01)

(52) U.S. Cl.
CPC ............ *A61M 5/165* (2013.01); *A61M 5/385* (2013.01); *A61M 39/10* (2013.01);
(Continued)

(58) Field of Classification Search
CPC .................. A61M 5/165; A61M 39/10; A61M 2005/1657; A61M 2205/7527;
(Continued)

(56) References Cited

U.S. PATENT DOCUMENTS

| 4,525,182 A | 6/1985 | Rising et al. | |
|---|---|---|---|
| 5,439,587 A * | 8/1995 | Stankowski | ......... B01D 36/001 96/219 |
| 5,622,626 A * | 4/1997 | Matkovich | ............. B01D 63/08 210/420 |

FOREIGN PATENT DOCUMENTS

| CN | 104083819 B | 5/2017 |
|---|---|---|
| EP | 0784988 A1 | 7/1997 |

(Continued)

OTHER PUBLICATIONS

Japanese Patent Application No. 2020-557952, First Office Action, Issued Nov. 15, 2022, OA Summary (translation), 2 pp.
(Continued)

*Primary Examiner* — Tasnim Mehjabin Ahmed
(74) *Attorney, Agent, or Firm* — Heslin Rothenberg Farley & Mesiti P.C.

(57) ABSTRACT

A filter for infusion medical lines including a flattened box-like body provided inside which is a plate-shaped element formed on whose one or both of the opposite faces are respective ribs defining inner channels. Arranged on the ribs are respective filtering hydrophilic membranes which separate the channels from respective interspaces delimited by a pair of half-shells. The interspaces are placed in communication with the inlet connector, the channels are placed in communication with the outlet fitting and the interspaces are placed in communication with the outside through vent openings arranged on the end walls of the box-like body.

9 Claims, 5 Drawing Sheets

(52) U.S. Cl.
CPC ............... *A61M 2005/1657* (2013.01); *A61M 2205/126* (2013.01); *A61M 2205/128* (2013.01); *A61M 2205/7527* (2013.01); *A61M 2205/7536* (2013.01)

(58) Field of Classification Search
CPC .... A61M 2205/7536; A61M 2205/126; A61M 2205/128; A61M 5/385
See application file for complete search history.

(56) References Cited

FOREIGN PATENT DOCUMENTS

| | | |
|---|---|---|
| EP | 1208857 A1 | 5/2002 |
| EP | 1421960 A1 | 5/2004 |
| GB | 2059776 A | 4/1981 |
| JP | S56100064 A | 8/1981 |
| JP | H9500809 A | 1/1997 |
| JP | H09502127 A | 3/1997 |
| JP | 2012192178 A | 10/2012 |
| WO | 9503842 A1 | 2/1995 |
| WO | 9506506 A1 | 3/1995 |
| WO | 9528215 A1 | 10/1995 |

OTHER PUBLICATIONS

International Search Report and Written Opinion of the International Searching Authority for International Application No. PCT/IB2019/052079 mailed on Jun. 11, 2019.

* cited by examiner

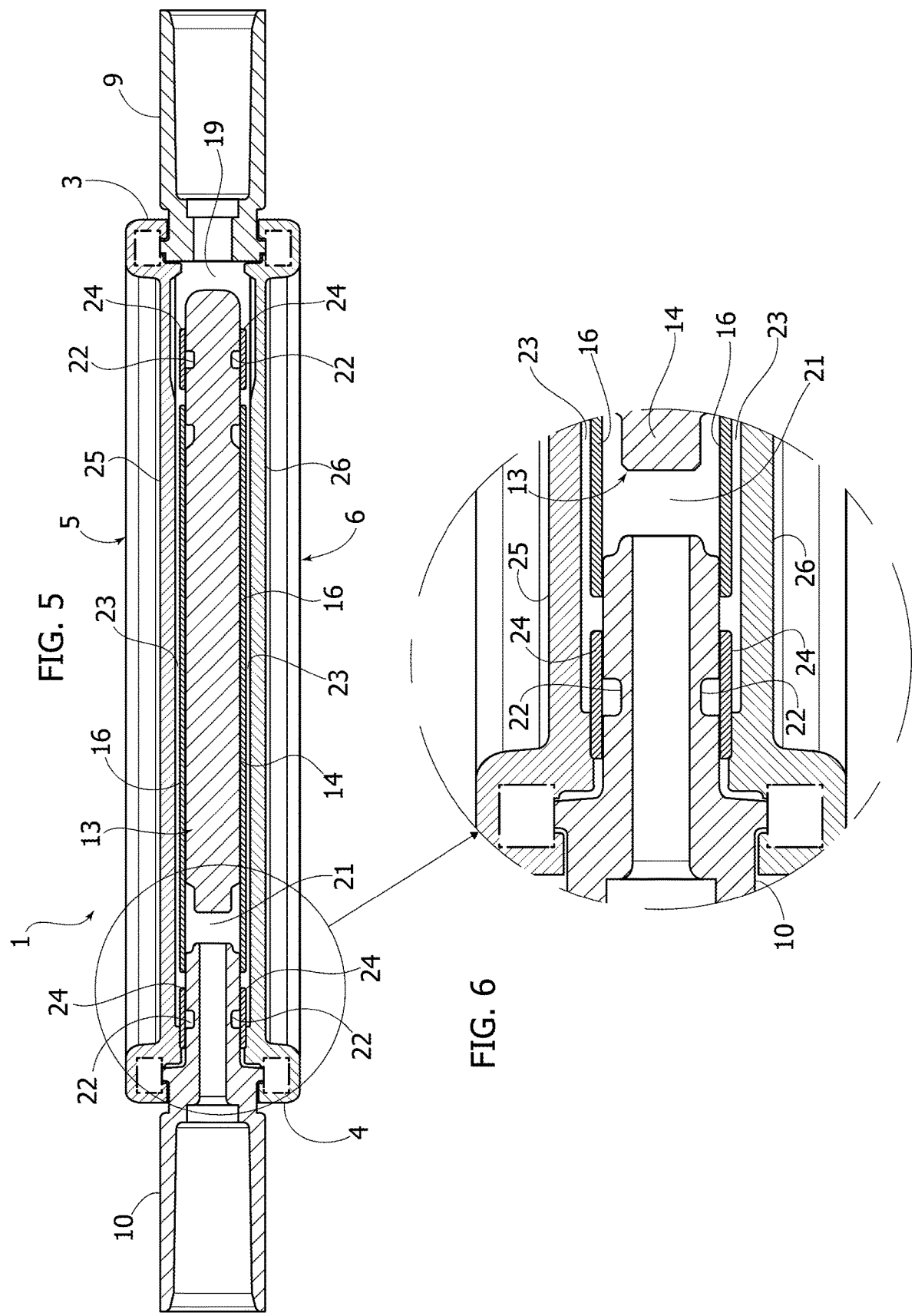

FILTER FOR INFUSION MEDICAL LINES

CROSS REFERENCE TO RELATED APPLICATIONS

This application is a national stage filing under section 371 of International Application No. PCT/IB2019/052079, filed on Mar. 14, 2019, published in English on Nov. 14, 2019 as WO2019/215516A1 and which claims priority to Italian Application No. 102018000005165, filed on May 8, 2018, the entire disclosure of these applications being hereby incorporated herein by reference.

FIELD OF THE INVENTION

The present invention regards a filter for infusion medical lines and more in particular an IV filter.

Filters thus made conventionally comprise a flattened box-like body having a first end wall and a second end wall, a pair of greater lateral walls, and a pair of smaller lateral walls. Such filters are provided with an inlet connector for a liquid to be filtered and an outlet connector for the filtered liquid at the one and the other end wall. Arranged in the box-like body is a plate-shaped element formed on whose at least one of the opposite faces is a plurality of ribs defining parallel channels. Arranged on the or on each plurality of ribs is a respective filtering hydrophilic membrane which separates the channels from one or from respective interspaces delimited by the two greater walls. The or each interspace is placed in communication with the inlet connector and the channels are placed in communication with the outlet connector. Furthermore, the or each interspace is placed in communication with the external by means of openings with associated hydrophobic membranes for deaerating the liquid.

STATE OF THE PRIOR ART

Documents EP-1208857, EP-1421960, U.S. Pat. Nos. 4,525,182 and 5,439,587 disclose filters thus made, wherein the deaeration openings provided with hydrophobic membranes are provided on the pair of greater lateral walls of the box-like body. Such positioning of the deaeration openings entails the drawback that they can be inadvertently occluded when handling the filter, or they can be unintentionally obstructed by objects present in proximity of the place of use of the filter, with the unacceptable risk of the liquid not being deaerated effectively.

Document WO 95/28215 describes a medical filter with multiple compartment comprising one or more vents each provided with a porous membrane for separating the air from the liquid. The vents are arranged at the ends of the box-like body but they are oriented perpendicularly to the greater faces of the filter, i.e. they terminate thereon, revealing the same drawbacks described above.

Document CN 104083819 describes a filter for medical lines having vent holes with respective membranes arranged in an end wall of the filter in proximity of the outlet connector for the liquid. The vent holes are placed in communication with a chamber designed to collect the liquid after it has been filtered by the hydrophilic membrane. The air venting is thus carried out only after filtering the liquid and it could be incomplete, in particular if the filter is used in a vertical position.

SUMMARY OF THE INVENTION

The object of the present invention is to overcome the aforementioned drawback.

With the aim of achieving such object, the invention regards a filter for infusion medical lines of the type defined in the preamble of claim 1 whose primary characteristic lies in the fact that the deaeration openings are provided on the end walls of the box-like body and so that—in use—the infusion liquid initially touches at least one of said hydrophobic membranes and subsequently touches and flows through said at least one hydrophilic membrane.

The hydrophobic membranes are arranged at the ends of the greater lateral walls of the plate-shaped element at respective transverse manifolds which are in turn placed in communication with the deaeration openings.

The inlet and outlet connectors for the liquid are conveniently coaxial so that—in use—torsional moments are not generated in the inflow and outflow tubes of the medical liquid.

The inlet and outlet connectors for the liquid can be designed for tube-tube or luer-tube or tube-luer or luer-luer connections of said medical line.

The or each filtering hydrophilic membrane can also be obtained as a single piece with the respective hydrophobic membranes.

The invention also regards a method for filtering and deaerating an infusion liquid for medical lines which provides for the use of a filter as claimed herein.

BRIEF DESCRIPTION OF THE DRAWINGS

Further characteristics and advantages of the invention will be apparent from the following detailed description, with reference to the attached drawings, provided by way of non-limiting example, wherein:

FIG. 5 is a longitudinal sectional view according to line A-A of FIG. 2, FIG. 6 is an enlargement of the portion of the filter in the circle of FIG. 5.

DETAINED DESCRIPTION OF THE INVENTION

Figure 1:
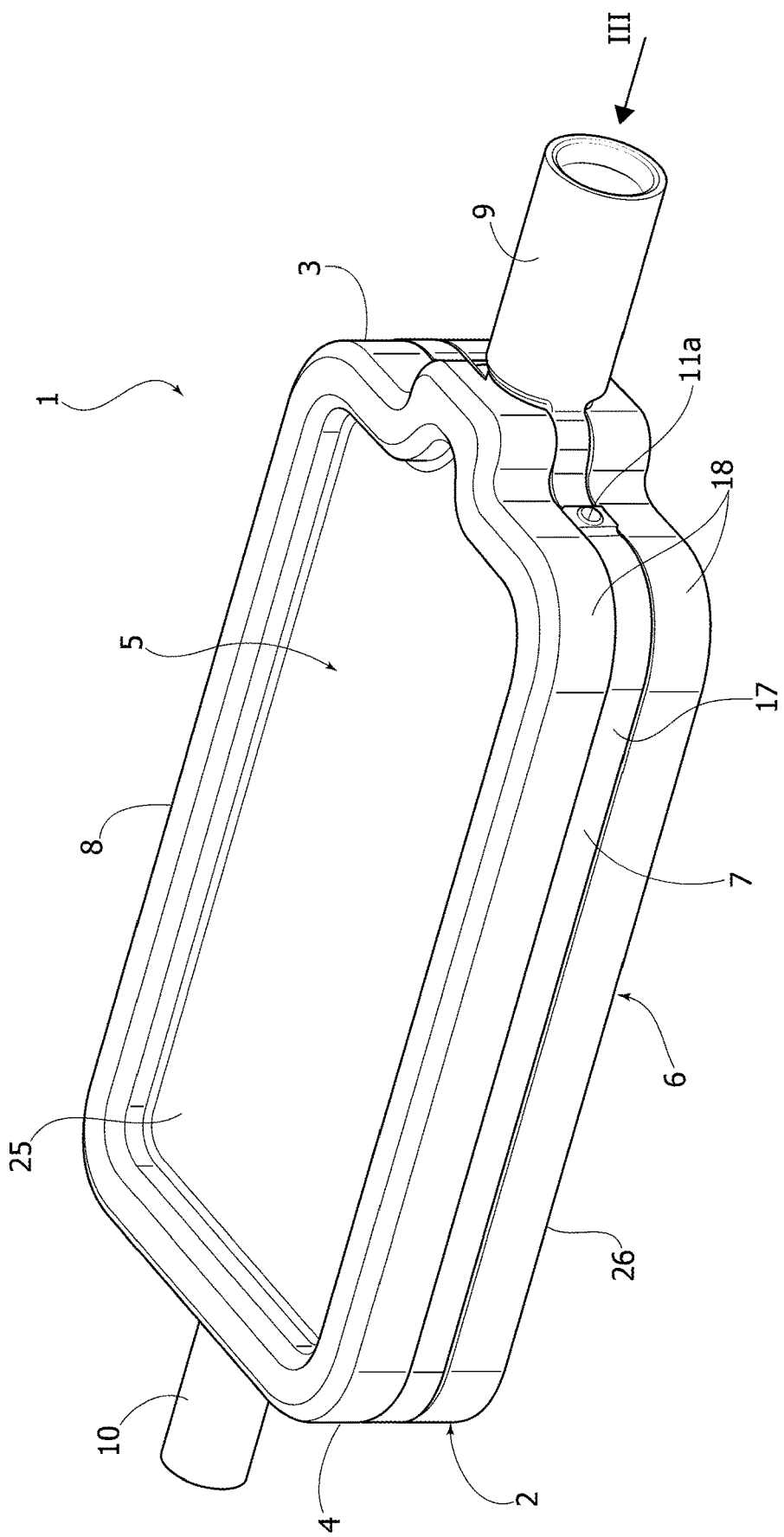
FIG. 1 is a schematic perspective view of an embodiment of the filter according to the invention.
Figure 2:
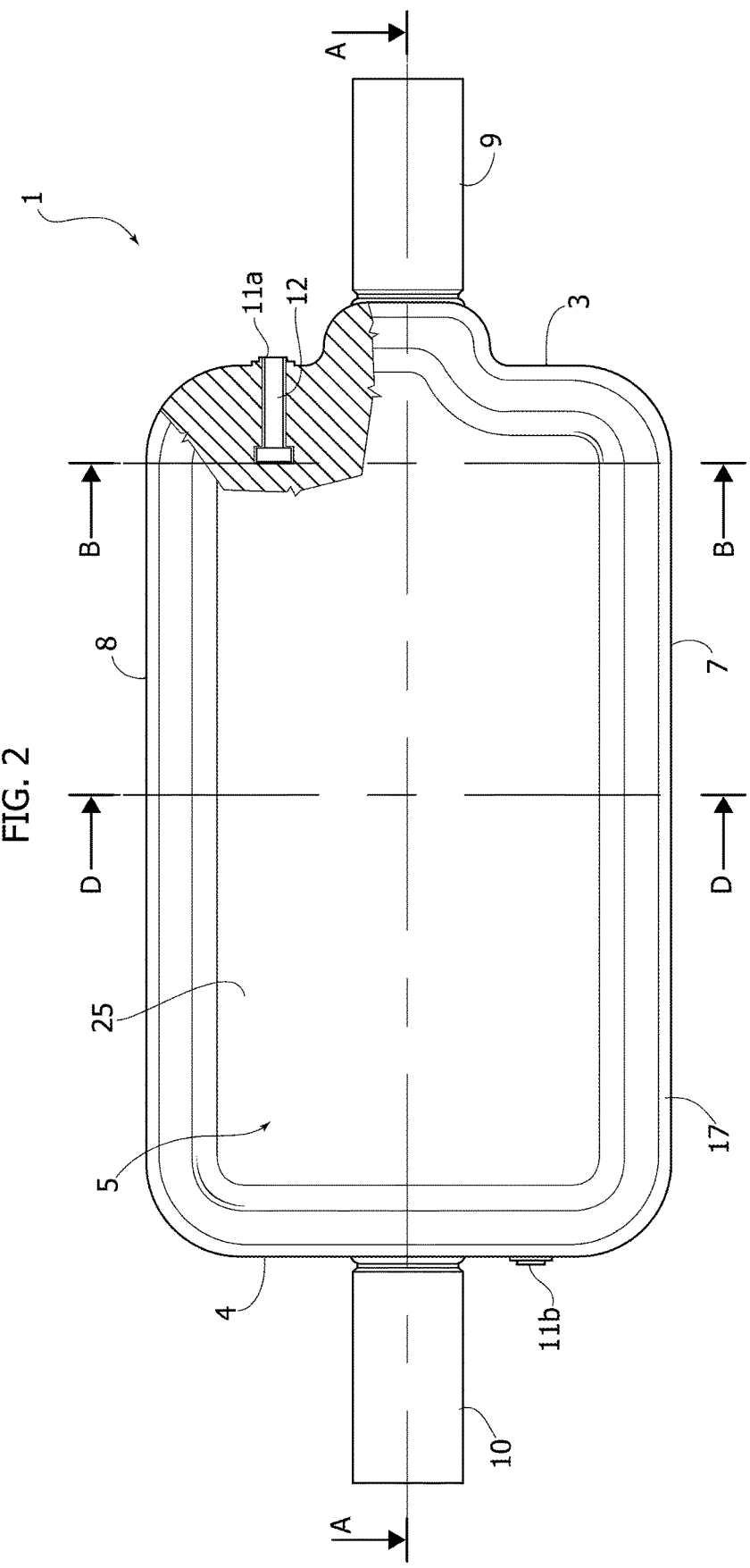
FIG. 2 is a plan and partially sectioned view of FIG. 1.
Figure 3:
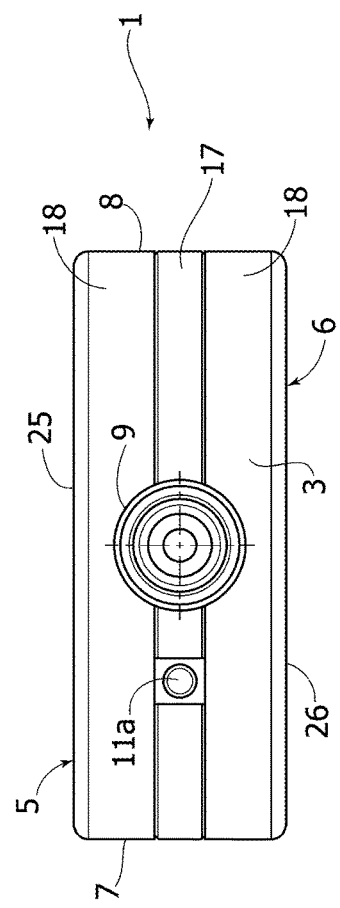
FIG. 3 is a front elevational view according to arrow III of FIG. 1.
Figure 4:
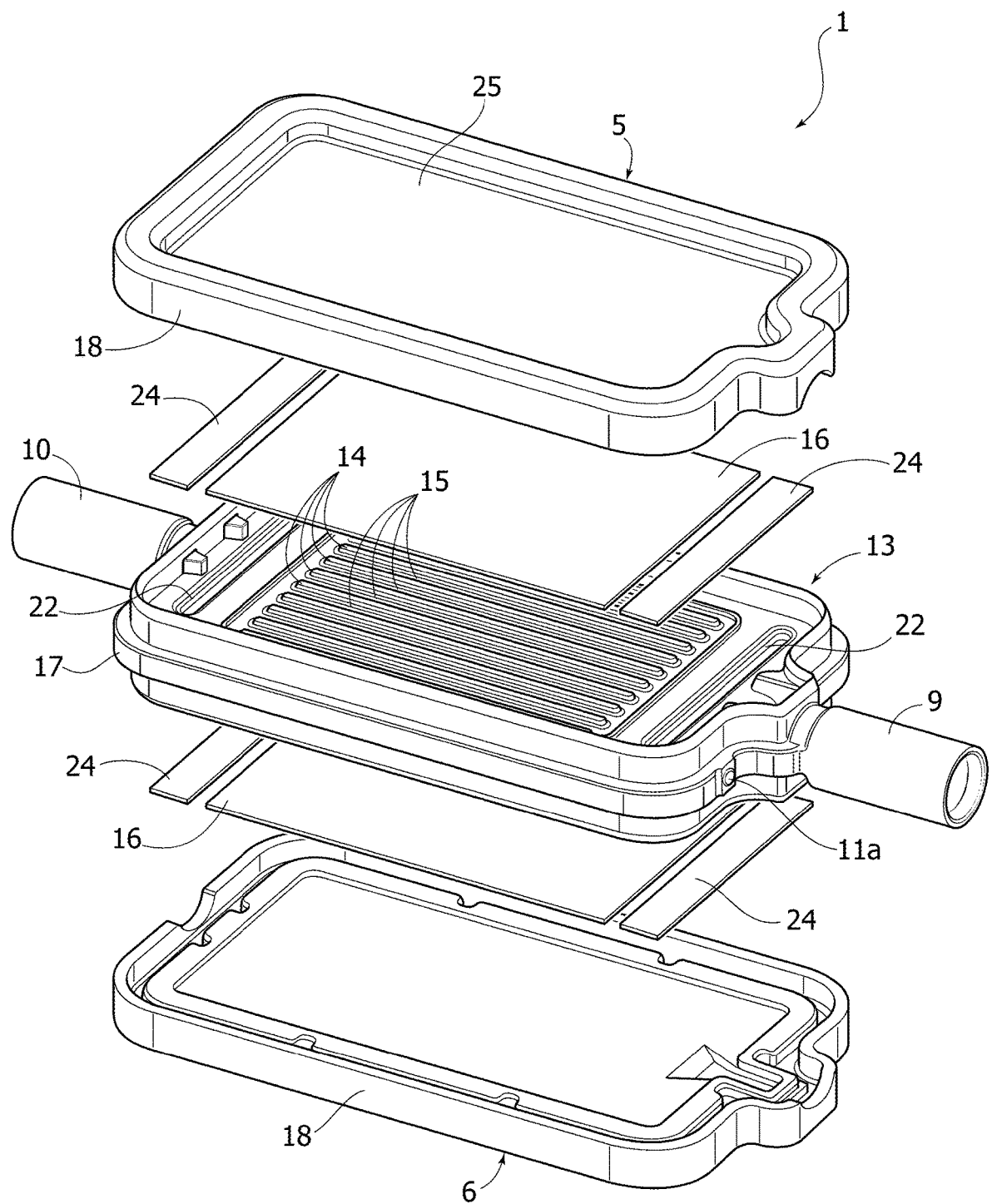
FIG. 4 is an exploded view of the filter of FIG. 1.
Figure 7:
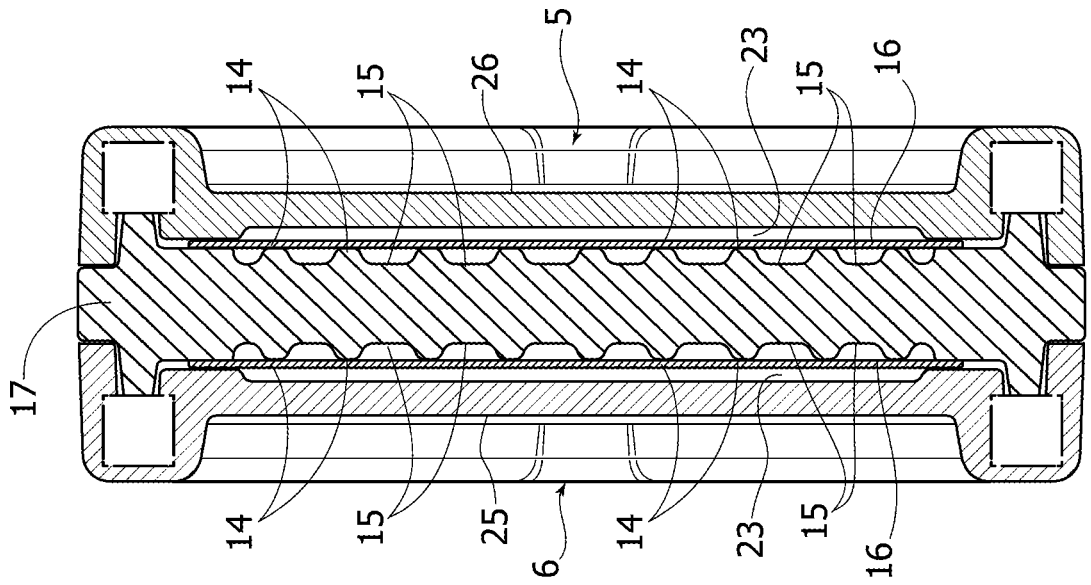
FIG. 7 is a cross-sectional view according to line B-B of FIG. 2.
Figure 8:
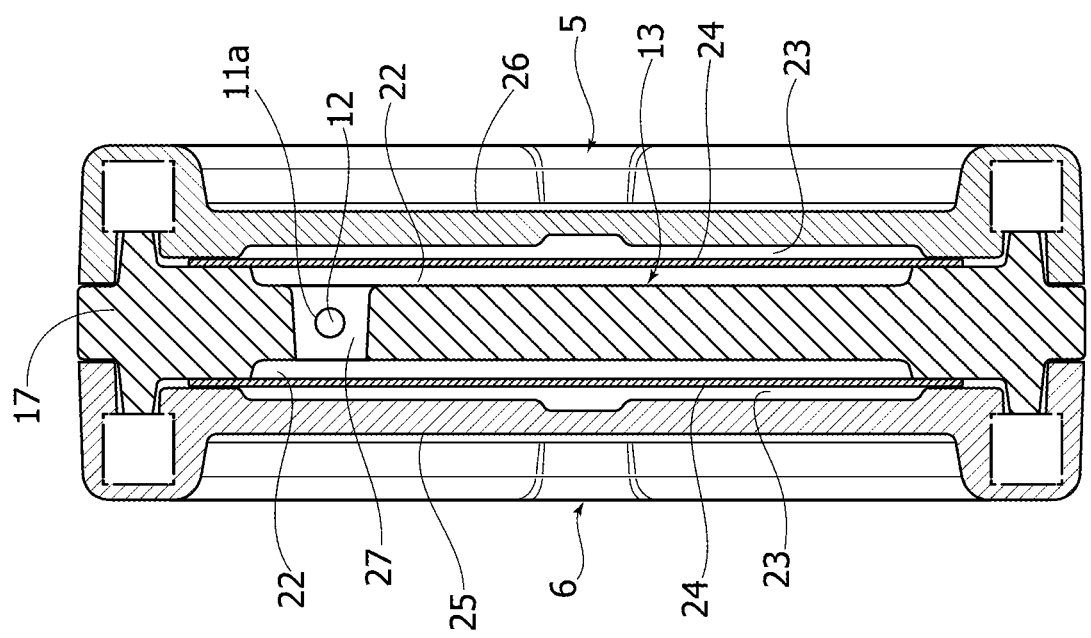
FIG. 8 is a cross-sectional view according to line D-D of FIG. 2.

Initially with reference to FIGS. 1-3, the infusion filter according to the invention is indicated in its entirety with 1.

It comprises a flattened box-like body 2 formed by a pair of half-shells 5, 6. The box-like body 2 comprises a first and second end wall 3, 4, a pair of greater lateral walls 25, 26, and a pair of smaller lateral walls 7, 8. Arranged at the first end wall 3 is an inlet connector 9 of a liquid to be filtered and arranged at the second end wall 4 is an outlet connector 10 for the filtered liquid. A first vent opening, in the form of a hole 11a, is provided for on the first end wall 3 in proximity of the inlet connector 9 and a second vent opening, in the form of a hole 11b, is provided on the second end wall 4 in proximity of the outlet connector 10.

Visible in the partial section of FIG. 2 is a duct 12 which connects the hole 11a with the internal of the box-like body 2. A similar duct not visible in the drawings connects the hole 11b with the internal of the box-like body 2.

Now, with reference to FIGS. 4 to 8 a plate-shaped element in the half-shells 5, 6 formed on whose opposite faces are respective pluralities of ribs 14 which define channels 15 extending longitudinally between the connectors 9, 10 is indicated with 13. Provided in proximity of the ends of the channels 15 of each face and perpendicularly thereto are transverse manifolds 22. The opposite manifolds 22 of each end of the plate-shaped element 13 are placed in communication with each other by means of respective passages of the plate-shaped element 13, one of which is indicated with 27 in FIG. 7, and furthermore they are placed in communication respectively with the vent hole 11a and with the vent hole 11b. Resting on each face of the plate-shaped element 13 is a respective hydrophilic membrane 16 which is welded to the plate-shaped element 13. Two pairs of hydrophobic membranes 24 are arranged above the four manifolds 22 and for example fixed by means of welding. The two pairs of hydrophobic membranes 24 can also be integrated and obtained as a single piece respectively with the one and with the other hydrophilic membrane 16.

The plate-shaped element 13 has a projecting perimeter edge 17 which is coupled with respective annular lips 18 of the half-shells 5, 6.

The inlet 9 and outlet 10 connectors for the liquid are coaxial to each other, are integrally joined to the plate-shaped element 13 and they can be configured for the tube-tube or luer-tube or tube-luer or luer-luer connections of the medical line.

FIGS. 5-8 show two interspaces 23, 23 coplanar to the faces of the plate-shaped element 13, separated by it by means of the respective hydrophilic membranes 16, 16 and each externally delimited by the respective half-shell 5, 6. A passage 19 (FIG. 5), provided on the plate-shaped element 13 at the end of the inlet connector 9 places both the interspaces 23, 23 in communication with such connector 9.

Referring more in detail with FIG. 6, a passage 21 of the plate-shaped element 13 places the outlet connector 10 in communication with the plurality of channels 15.

As clear from the above, the filter 1 according to the invention has a configuration that is compact and small in size.

During use, the infusion liquid—through the inlet connector 9 and the passage 19—enters into the interspaces 23, 23 initially touching the proximal hydrophobic membranes 24, 24 which allow the air trapped in the liquid to flow out into the respective manifolds 22 before being dispersed outside the filter 1 through the duct 12 and the hole 11a.

Subsequently, the fluid touches and flows through the filtering hydrophilic membrane 16, 16 so as to be conveyed from the channels 15 towards the passage 21 and flow out through the outlet connector 10.

The filter 1 according to the invention is normally used in a vertical portion of an infusion line, i.e. it is oriented so that the inlet connector 9 is positioned at the upper part with respect to the outlet connector 10. After touching the proximal hydrophobic membranes 24, should the liquid still contain air, for example due to the orientation of use different from the one described previously, the residual air can flow out through the distal membranes 24 and the respective manifolds 22 connected to the hole 11b.

The arrangement of the hydrophobic membranes 24 upstream and downstream of the flow in the interspaces 23 of the filter 1 reveals the further advantage lying in the fact that, in particular during the priming, the air contained in the liquid accumulates in the end areas of the filter 1 so as not to occlude part of the filtering surfaces; in this manner, the air has more time to flow out with respect to the known solutions described previously.

Obviously, the construction details and the embodiments may widely vary with respect to what has been described and illustrated, without departing from the scope of protection of the present invention as defined in the claims that follow. Thus, for example, the filter could generally have a different shape with respect to the one represented in the drawings and it could also be provided with a single filtering hydrophilic membrane 16 arranged on ribs 14 formed on only one of the faces of the plate-shaped element 13.

The invention claimed is:

1. A filter for infusion medical lines comprising:
   a flattened box-like body including a pair of half-shells and a plate-shaped element therebetween, the flattened box-like body provided with an inlet connector for an infusion liquid to be filtered and an outlet connector for the infusion liquid,
   the flattened box-like body comprising a first end wall and a second end wall, the first end wall and the second end wall comprising opposing longitudinal faces, said inlet connector located on a first longitudinal face of said opposing longitudinal faces and said outlet connector located on a second longitudinal face of said opposing longitudinal faces,
   wherein the plate-shaped element includes opposing sides and ribs formed on at least one opposing side of the opposing sides, said ribs defining inner channels parallelly extending between said inlet connector and said outlet connector,
   at least one filtering hydrophilic membrane arranged on said ribs, said at least one filtering hydrophilic membrane separating said channels from an interspace delimited by a corresponding half-shell of the pair of half-shells, said interspace being placed in communication with the inlet connector and said channels communicating with the outlet connector, and said interspace further being placed in communication with the outside through vent openings with associated hydrophobic membranes,
   and wherein said vent openings are arranged on said opposing longitudinal faces of the box-like body; and
   as the infusion liquid travels in a direction from the inlet connector towards the outlet connector, the infusion liquid initially touches at least one of said hydrophobic membranes and subsequently touches and flows through said at least one filtering hydrophilic membrane.

2. The filter according to claim 1, wherein said channels are provided on both opposing sides of said plate-shaped element and a pair of filtering hydrophilic membranes separate said channels from a pair of interspaces each delimited by a respective half-shell of the pair of half-shells.

3. The filter according to claim 1, at the ends of the opposing sides of the plate-shaped element there are provided transverse manifolds on which said hydrophobic membranes are arranged, said transverse manifolds being placed in communication with said vent openings.

4. The filter according to claim 1, wherein said inlet connector and said outlet connector are coaxial.

5. The filter according to claim 1, wherein said inlet connector and said outlet connector are designed for tube-tube or luer-tube or tube-luer or luer-luer connections of said medical line.

6. The filter according to claim 1, wherein a filtering hydrophilic membrane of the at least one filtering hydrophilic membrane is made of one piece with said hydrophobic membranes.

7. The filter according to claim 1, wherein the hydrophobic membranes include a first hydrophobic membrane and a second hydrophobic membrane, and wherein the at least one filtering hydrophilic membrane is located between the first hydrophobic membrane and the second hydrophobic membrane.

8. The filter according to claim 7, wherein the first hydrophobic membrane is disposed towards the inlet connector and the second hydrophobic membrane is disposed towards the outlet connector such that, as the infusion liquid travels in the direction from the inlet connector towards the outlet connector, the infusion liquid necessarily contacts at least one of the hydrophobic membranes prior to contacting the at least one filtering hydrophilic membrane.

9. A filter for infusion medical lines comprising:
a flattened box-like body including a pair of half-shells and a plate-shaped element therebetween, the flattened box-like body provided with an inlet connector for an infusion liquid to be filtered and an outlet connector for the infusion liquid,
said inlet connector and said outlet connector being provided respectively at a first end wall and at a second end wall of the flattened box-like body, the first end wall and the second end wall comprising opposing longitudinal faces,
wherein the plate-shaped element includes opposing sides and ribs formed on at least one opposing side of the opposing sides, said ribs defining inner channels parallelly extending between said inlet connector and said outlet connector,
at least one filtering hydrophilic membrane arranged on said ribs, said at least one filtering hydrophilic membrane separating said channels from an interspace delimited by a corresponding half-shell of the pair of half-shells, said interspace being placed in communication with the inlet connector and said channels communicating with the outlet connector, and said interspace further being placed in communication with the outside through vent openings with associated hydrophobic membranes,
and wherein said vent openings are arranged on said opposing longitudinal faces of the box-like body; and
as the infusion liquid travels in a direction from the inlet connector towards the outlet connector, the infusion liquid initially touches at least one of said hydrophobic membranes and subsequently touches and flows through said at least one filtering hydrophilic membrane;
wherein the hydrophobic membranes include a first hydrophobic membrane and a second hydrophobic membrane, and wherein the at least one filtering hydrophilic membrane is located between the first hydrophobic membrane and the second hydrophobic membrane;
wherein the first hydrophobic membrane is disposed towards the inlet connector and the second hydrophobic membrane is disposed towards the outlet connector such that, as the infusion liquid travels in the direction from the inlet connector towards the outlet connector, the infusion liquid necessarily contacts at least one of the hydrophobic membranes prior to contacting the at least one filtering hydrophilic membrane.

* * * * *